US012677795B2

(12) United States Patent
Yoshinaga

(10) Patent No.: US 12,677,795 B2
(45) Date of Patent: Jul. 14, 2026

(54) EXCREMENT TREATMENT MATERIAL, AND METHODS FOR MANUFACTURING AND UTILIZING THE SAME

(71) Applicant: DAIKI CO., LTD., Tokyo (JP)

(72) Inventor: Junji Yoshinaga, Tokyo (JP)

(73) Assignee: DAIKI CO., LTD., Tokyo (JP)

( * ) Notice: Subject to any disclaimer, the term of this patent is extended or adjusted under 35 U.S.C. 154(b) by 898 days.

(21) Appl. No.: 17/191,500

(22) Filed: Mar. 3, 2021

(65) Prior Publication Data

US 2021/0204507 A1 Jul. 8, 2021

Related U.S. Application Data

(63) Continuation of application No. PCT/JP2019/029600, filed on Jul. 29, 2019.

(30) Foreign Application Priority Data

Oct. 4, 2018 (JP) ................................. 2018-188819

(51) Int. Cl.
   *A01K 1/015* (2006.01)
   *A61L 9/013* (2006.01)
(52) U.S. Cl.
   CPC ............ *A01K 1/0155* (2013.01); *A61L 9/013* (2013.01)
(58) Field of Classification Search
   CPC .. A01K 1/0155; A01K 1/0154; A01K 1/0152; A61L 9/013; B65D 81/24; B65D 81/28
   See application file for complete search history.

(56) References Cited

U.S. PATENT DOCUMENTS

| | | | | | |
|---|---|---|---|---|---|
| 4,448,151 | A | * | 5/1984 | Lowe ................... | A01K 1/0107 |
| | | | | | 119/165 |
| 4,774,907 | A | * | 10/1988 | Yananton ............. | A01K 1/0155 |
| | | | | | 119/169 |
| 5,850,798 | A | * | 12/1998 | Engel ................... | A01K 1/0107 |
| | | | | | 119/170 |
| 6,089,190 | A | | 7/2000 | Jaffee et al. | |
| 8,869,745 | B1 | * | 10/2014 | Stepanek ............. | A01K 1/0107 |
| | | | | | 119/169 |
| 2008/0135161 | A1 | * | 6/2008 | Bohanan ................ | B65D 81/24 |
| | | | | | 156/227 |
| 2010/0307422 | A1 | * | 12/2010 | Huck ................... | A01K 1/0107 |
| | | | | | 600/584 |

(Continued)

FOREIGN PATENT DOCUMENTS

| | | |
|---|---|---|
| JP | H04-132556 A | 5/1992 |
| JP | 2010-158253 A | 7/2010 |

(Continued)

OTHER PUBLICATIONS

Oct. 15, 2019 Written Opinion issued in International Patent Application No. PCT/JP2019/029600.

(Continued)

*Primary Examiner* — Trinh T Nguyen
(74) *Attorney, Agent, or Firm* — Oliff PLC

(57) ABSTRACT

An excrement treatment material includes a plurality of grains, and a packaging bag. The grains are grains for treating excrement. The plurality of grains are housed in the packaging bag. The packaging bag is provided with odor eliminating property or deodorizing property.

17 Claims, 4 Drawing Sheets

(56) References Cited

U.S. PATENT DOCUMENTS

2016/0113232 A1 * 4/2016 Thompson .............. A01K 1/01
119/172

FOREIGN PATENT DOCUMENTS

| JP | 2014-018694 A | 2/2014 | |
|----|----|----|----|
| JP | 2014-103864 A | 6/2014 | |
| JP | 2015-097996 A | 5/2015 | |
| JP | 2016-041038 A | 3/2016 | |
| JP | 2016-208975 A | 12/2016 | |
| JP | 6300994 * | 3/2018 | ........... A01K 1/0155 |
| KR | 20090068428 * | 6/2009 | ............ B65D 81/24 |
| TW | M313111 U | 6/2007 | |

OTHER PUBLICATIONS

May 1, 24, 2022 Office Action issued in Chinese Patent Application No. 201980065403.5.
Dec. 1, 2022 Office Action issued in Chinese Patent Application No. 201980065403.5.
Apr. 14, 2023 Office Action issued in Chinese Patent Application No. 201980065403.5.
Ding Hao, "Nano antibacterial technology", Kogyo Publish Co. Ltd., Oct. 31, 2017, pp. 331-332.
Sha Mei, "Supply Chain Management and Logistics" Shanghai Jiao Tong University, Mar. 31, 2010, p. 117.
Wu Qiang, "Logistics Equipment and Technology", Wuhan University of Technology, Jan. 31, 2013, pp. 150-151.

* cited by examiner

EXCREMENT TREATMENT MATERIAL, AND METHODS FOR MANUFACTURING AND UTILIZING THE SAME

CROSS REFERENCE TO RELATED APPLICATION

This is a Continuation of International Application No. PCT/JP2019/029600 filed Jul. 29, 2019, which claims the benefit of Japanese Application No. 2018-188819 filed Oct. 4, 2018. The contents of these applications are hereby incorporated by reference in their entirety.

TECHNICAL FIELD

The present invention relates to an excrement treatment material, and methods for manufacturing and utilizing the same.

BACKGROUND ART

A conventional excrement treatment material is disclosed in, for example, Patent Document 1. The excrement treatment material disclosed in Patent Document 1 includes a plurality of grains that absorb and treat human or animal excrement. These grains are shipped in a state of being housed collectively in one packaging bag.

CITATION LIST

Patent Document

Patent Document 1: JP 2010-158253A

SUMMARY OF INVENTION

Technical Problem

In the excrement treatment material described above, used grains are, for example, disposed of in a garbage box or the like as a household garbage. However, an odor generates from excrement adhering to the used grains (including excrement absorbed in the grains), and the odor sometimes diffuses around the garbage box or the like. This has been a factor in giving discomfort to users of the excrement treatment material.

Solution to Problem

The present invention has been made in view of the above-described problem, and it is an object thereof to provide an excrement treatment material that is suitable for making an odor less likely to diffuse around after disposal, and methods for manufacturing and utilizing the same.

An excrement treatment material according to the present invention includes: a plurality of grains for treating excrement; and a packaging bag in which the plurality of grains are housed. The packaging bag is provided with odor eliminating property or deodorizing property.

In this excrement treatment material, the packaging bag is provided with odor eliminating property or deodorizing property. For this reason, by disposing of used grains in a garbage box or the like in a state in which the grains are housed in the packaging bag, it is possible to reduce an odor generating from excrement adhering to the grains while confining the odor in the packaging bag. Thus, the odor becomes less likely to diffuse around.

A method for manufacturing an excrement treatment material according to the present invention includes: a grain forming step of forming a plurality of grains for treating excrement; and a grain housing step of housing the plurality of grains formed in the grain forming step in a packaging bag. The packaging bag is provided with odor eliminating property or deodorizing property.

In this manufacturing method, the packaging bag, which is provided with odor eliminating property or deodorizing property, is used. For this reason, in the manufactured excrement treatment material, by disposing of used grains in a garbage box or the like in a state in which the grains are housed in the packaging bag, it is possible to reduce an odor generating from excrement adhering to the grains while confining the odor in the packaging bag. Thus, the odor becomes less likely to diffuse around.

A method for utilizing an excrement treatment material according to the present invention is a method for utilizing the above-described excrement treatment material, and includes: an excrement treating step of taking out the plurality of grains from the packaging bag to use the plurality of grains for treatment of the excrement; and a grain re-housing step of housing the plurality of grains that have been used in the excrement treating step in the packaging bag again.

In this utilizing method, the grains, which have been taken out from the packaging bag to be used for treatment of the excrement, are housed again in the packaging bag provided with odor eliminating property or deodorizing property. By disposing of used grains in a garbage box or the like in a state in which the grains are housed in the packaging bag in this way, it is possible to reduce an odor generating from excrement adhering to the grains while confining the odor in the packaging bag. Thus, the odor becomes less likely to diffuse around.

Advantageous Effects of Invention

According to the present invention, it is possible to implement an excrement treatment material that is suitable for making an odor less likely to diffuse around after disposal, and methods for manufacturing and utilizing the same.

BRIEF DESCRIPTION OF DRAWINGS

FIG. 5 is a schematic view showing an end face along a line V-V in

FIG. 4.

DESCRIPTION OF EMBODIMENTS

Figure 1:
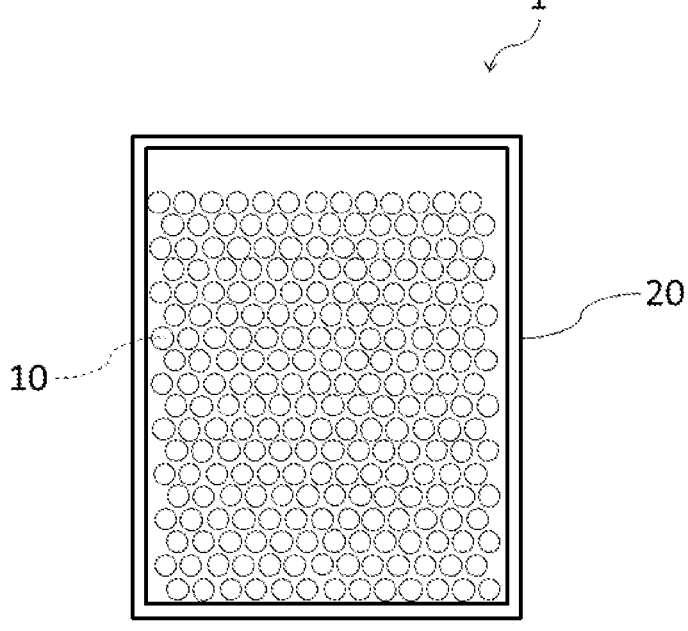
FIG. 1 is a front view showing a first embodiment of an excrement treatment material according to the present invention.

Hereinafter, embodiments of the present invention will be described in detail with reference to the drawings. In the description of the drawings, the same elements are given the same reference numerals, and a redundant description will be omitted.

First Embodiment

FIG. 1 is a front view showing a first embodiment of an excrement treatment material according to the present invention. An excrement treatment material 1 is an excrement treatment material used for treating excrement, and includes a plurality of grains 10, and a packaging bag 20. In FIG. 1, for ease of viewing, the packaging bag 20 is shown being made transparent. The excrement treatment material 1 may be an excrement treatment material for humans that treats excrement of humans, or may be an excrement treatment material for animals that treats excrement of animals such as cats or dogs.

Figure 2:
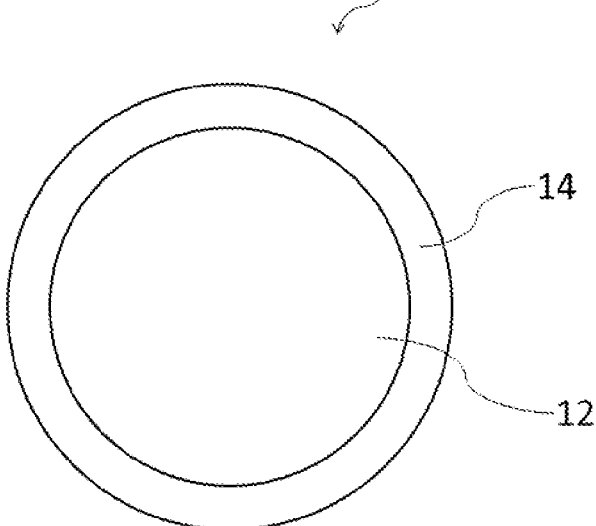
FIG. 2 is a schematic view showing a grain 10.

FIG. 2 is a schematic view showing the grain 10. The grains 10 are grains for treating excrement. In the present embodiment, the grains 10 treat excrement by absorbing the excrement. The particle diameter of the grains 10 is, for example, about 5 to 15 mm. Each grain 10 has a core portion 12 and a coating portion 14. The core portion 12 is formed into a granular shape. Examples of such a granular shape include a sphere, a cylinder, and an ellipsoid. The core portion 12 has a function of absorbing and retaining moisture of the excrement. The core portion 12 preferably has an organic matter as a main material. As used herein, the main material of the core portion 12 refers to one of the material(s) constituting the core portion 12 that accounts for the highest weight ratio in the core portion 12. As the organic matter, for example, papers, used tea leaves, plastics, or bean curd lees can be used.

The papers refer to a material composed mainly of pulp. Examples of the papers include, in addition to ordinary paper, a vinyl chloride wallpaper classified product (paper obtained by classifying vinyl chloride wallpaper), fluff pulp, papermaking sludge, and pulp sludge. As the plastics, a disposable diaper classified product (plastic obtained by classifying disposable diapers), for example, may be used. The bean curd lees are preferably dried bean curd lees.

The coating portion 14 covers the core portion 12. The coating portion 14 may cover the entire surface of the core portion 12, or may cover only a part of the surface of the core portion 12. The coating portion 14 has a function of bonding the grains 10 that have absorbed excrement when in use, and clumping them together. The coating portion 14 contains an adhesive material. As the adhesive material, it is possible to use, for example, starch, CMC (carboxymethyl cellulose), PVA (polyvinyl alcohol), dextrin, or a water-absorbent polymer. The coating portion 14 also preferably has the organic matter as a main material.

Returning to FIG. 1, the plurality of grains 10 are housed in the packaging bag 20. The packaging bag 20 is provided with odor eliminating property or deodorizing property. That is, the packaging bag 20 may be provided with both of the odor eliminating property and the deodorizing property, or may be provided with only either one of the odor eliminating property or the deodorizing property. In the present embodiment, the packaging bag 20 is made of a raw material that contains an odor eliminating agent or a deodorizing agent. The raw material preferably contains a metal (including a metal ion) that functions as the odor eliminating agent, or a porous material that functions as the deodorizing agent. For example, the raw material can be constituted by mixing the metal or the porous material into a plastic.

As the above-described metal, it is possible to use, for example, copper, silver, zinc, titanium, or the like. The above-described porous material may be organic matter, or may be inorganic matter. Examples of the porous material of organic matter include coffee-extracted grounds, used tea leaves, and activated carbon. Examples of the porous material of inorganic matter include silica gel, and bentonite.

Next, an example of a method for manufacturing the excrement treatment material 1 will be described as a first embodiment of a method for manufacturing an excrement treatment material according to the present invention. This manufacturing method includes a grain forming step, and a grain housing step.

The grain forming step is a step of forming the plurality of grains 10. The grain forming step includes a core portion forming step and a coating portion forming step. The core portion forming step is a step of forming a plurality of the core portions 12. In this step, granules that will serve as the core portions 12 are formed by granulating a core portion material (material(s) constituting the core portion 12) with a granulation apparatus. As the granulation apparatus, for example, an extrusion granulator can be used. Prior to the granulation, the core portion material is subjected to pretreatment such as pulverization, kneading, and adding water, as needed.

The coating portion forming step is a step of forming the coating portion 14. In this step, the coating portion 14 is formed by attaching a powdery coating material (materials constituting the coating portion 14) to the surface of each of the core portions 12 with a coating apparatus or the like. The coating material can be attached by, for example, sprinkling or spraying. Thus, the plurality of grains 10 that have a double-layer structure composed of the core portion 12 and the coating portion 14 are obtained.

The grain housing step is a step of housing the plurality of grains 10 formed in the grain forming step in the packaging bag 20. In this step, a predetermined amount (e.g. 7 liters) of the grains 10 is housed in the packaging bag 20 in a state that the upper end portion of the packaging bag 20 is open with a filling machine or the like. The packaging bag 20 is provided with the odor eliminating property or the deodorizing property by being made of the raw material that contains the odor eliminating agent or the deodorizing agent as described above. After that, the packaging bag 20 is sealed by closing the upper end portion of the packaging bag 20. Accordingly, the excrement treatment material 1 is obtained.

Furthermore, an example of a method for utilizing the excrement treatment material 1 will be described as an embodiment of a method for utilizing an excrement treatment material according to the present invention. This utilizing method includes an excrement treating step, and a grain re-housing step.

The excrement treating step is a step of taking out the plurality of grains 10 from the packaging bag 20 to use the plurality of grains 10 for treatment of excrement. In this step, for example, after the plurality of grains 10 are taken out by opening the packaging bag 20, the grains 10 are placed in a box-shaped toilet so that humans or animals can excrete on the grains 10.

The grain re-housing step is a step of housing the plurality of grains 10 that have been used in the excrement treating step in the packaging bag 20 again. In this step, for example, the used grains 10, namely the grains 10 that have received excrement are picked up from the toilet and put back into the packaging bag 20 with a scoop or the like. After that, the packaging bag 20 is preferably sealed again by a method such as binding the opening of the packaging bag 20. Thus, the used grains 10 can be disposed of in a state of being housed in the packaging bag 20.

Advantageous effects of the present embodiment will be described. In the present embodiment, the packaging bag 20, which is provided with odor eliminating property or deodorizing property, is used. For this reason, in the excrement treatment material 1, by disposing of used grains 10 in a garbage box or the like in a state in which the grains 10 are housed in the packaging bag 20, it is possible to reduce an odor generating from excrement adhering to the grains 10 while confining the odor in the packaging bag 20. Thus, the odor becomes less likely to diffuse around. Accordingly, the excrement treatment material 1 that is suitable for making an odor less likely to diffuse around after disposal, and methods for manufacturing and utilizing the same are implemented.

The packaging bag 20 is made of the raw material that contains an odor eliminating agent or a deodorizing agent. Thus, it is possible to implement the packaging bag 20 that is provided with the odor eliminating property or the deodorizing property without particularly processing the packaging bag 20.

In the case where the raw material contains the metal that functions as the odor eliminating agent, the packaging bag 20 can be provided with excellent odor eliminating property. In the case where copper is used as the metal, it is especially advantageous in persistence of the odor eliminating property, safety, and inexpensiveness.

In the case where the raw material contains the porous material that functions as the deodorizing agent, the packaging bag 20 can be provided with excellent deodorizing property. In the case where the porous material is organic matter, it is possible to obtain the packaging bag 20 suitable for being disposed of by incineration. In the case where coffee-extracted grounds or used tea leaves are used as the porous material, it is especially advantageous in persistence of the deodorizing property, safety, and inexpensiveness.

Second Embodiment

Figure 3:
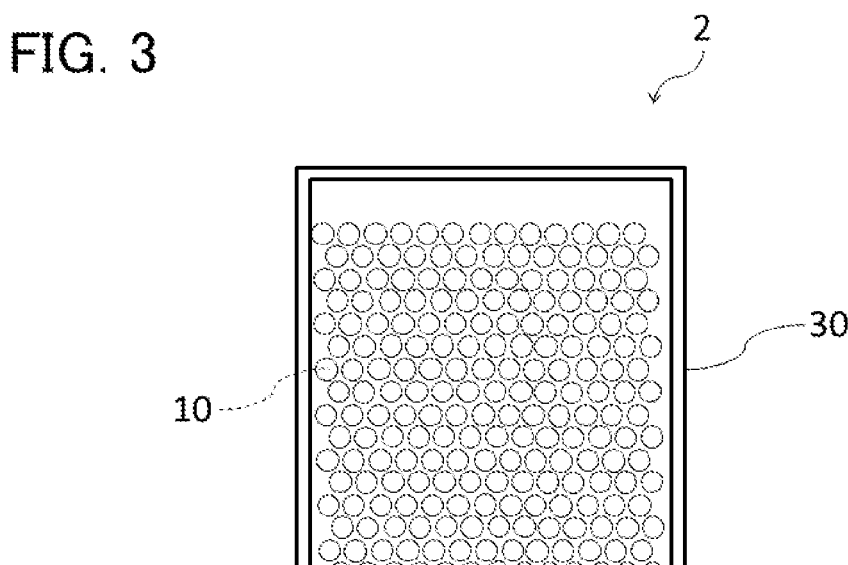
FIG. 3 is a front view showing a second embodiment of the excrement treatment material according to the present invention.

FIG. 3 is a front view showing a second embodiment of the excrement treatment material according to the present invention. An excrement treatment material 2 is an excrement treatment material used for treating human or animal excrement, and includes the plurality of grains 10, and a packaging bag 30. In FIG. 3, for ease of viewing, the packaging bag 30 is shown being made transparent. The constitution of the grains 10 is as described in the first embodiment.

The plurality of grains 10 are housed in the packaging bag 30. The packaging bag 30 is provided with odor eliminating property or deodorizing property. In the present embodiment, an odor eliminating agent or a deodorizing agent adheres to the inner surface of the packaging bag 30. As the odor eliminating agent or the deodorizing agent, respectively, the metal or the porous material described above can be used. Note that the packaging bag 30 may be made of a raw material that contains an odor eliminating agent or a deodorizing agent similarly with the packaging bag 20.

Next, an example of a method for manufacturing the excrement treatment material 2 will be described as a second embodiment of the method for manufacturing an excrement treatment material according to the present invention. This manufacturing method includes a grain forming step, an inner surface processing step, and a grain housing step. The contents of the grain forming step are as described in the first embodiment.

The inner surface processing step is a step of making the odor eliminating agent or the deodorizing agent adhere to the inner surface of the packaging bag 30 prior to the grain housing step. In this step, for example, a powdery odor eliminating agent or a powdery deodorizing agent is attached to the inner surface of the packaging bag 30 by being applied on the inner surface after the odor eliminating agent or the deodorizing agent is mixed with an adhesive. Note that the grain forming step and the inner surface processing step may be performed in arbitrary order. That is, either one of the both steps may be performed prior to the other, or the both steps may be performed simultaneously.

The grain housing step is a step of housing the plurality of grains 10 formed in the grain forming step in the packaging bag 30. In this step, a predetermined amount of the grains 10 is housed in the packaging bag 30 in a state that the upper end portion of the packaging bag 30 is open with a filling machine or the like. The packaging bag 30 is provided with the odor eliminating property or the deodorizing property by attaching the odor eliminating agent or the deodorizing agent to the inner surface thereof as described above. After that, the packaging bag 30 is sealed by closing the upper end portion of the packaging bag 30. Accordingly, the excrement treatment material 2 is obtained. The excrement treatment material 2 can be utilized in the same way as the excrement treatment material 1.

Advantageous effects of the present embodiment will be described. In the present embodiment, the packaging bag 30, which is provided with odor eliminating property or deodorizing property, is used. For this reason, in the excrement treatment material 2, by disposing of used grains 10 in a garbage box or the like in a state in which the grains 10 are housed in the packaging bag 30, it is possible to reduce an odor generating from excrement adhering to the grains 10 while confining the odor in the packaging bag 30. Thus, the odor becomes less likely to diffuse around. Accordingly, the excrement treatment material 2 that is suitable for making an odor less likely to diffuse around after disposal, and methods for manufacturing and utilizing the same are implemented.

An odor eliminating agent or a deodorizing agent adheres to the inner surface of the packaging bag 30. Thus, it is possible to implement the packaging bag 30 that is provided with the odor eliminating property or the deodorizing property without using a raw material that contains an odor eliminating agent or a deodorizing agent as the raw material of the packaging bag 30. Also, in the case where the packaging bag 30 is made of the raw material that contains an odor eliminating agent or a deodorizing agent, it is possible to enhance the odor eliminating property or the deodorizing property of the packaging bag 30.

The inner surface processing step is performed prior to the grain housing step. By performing the inner surface processing step before the grains 10 are housed in the packaging bag 30 in this way, the odor eliminating agent or the deodorizing agent can be attached to the inner surface of the packaging bag 30 efficiently without being obstructed by the grains 10. Other effects of the excrement treatment material 2 are the same as the excrement treatment material 1.

Third Embodiment

Figure 4:
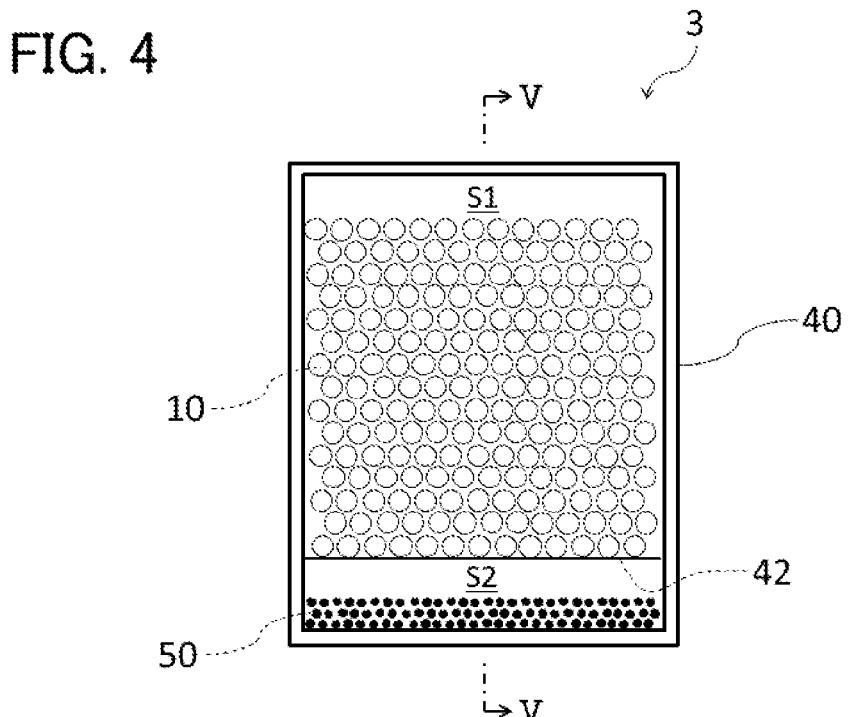
FIG. 4 is a front view showing a third embodiment of the excrement treatment material according to the present invention.
Figure 5:
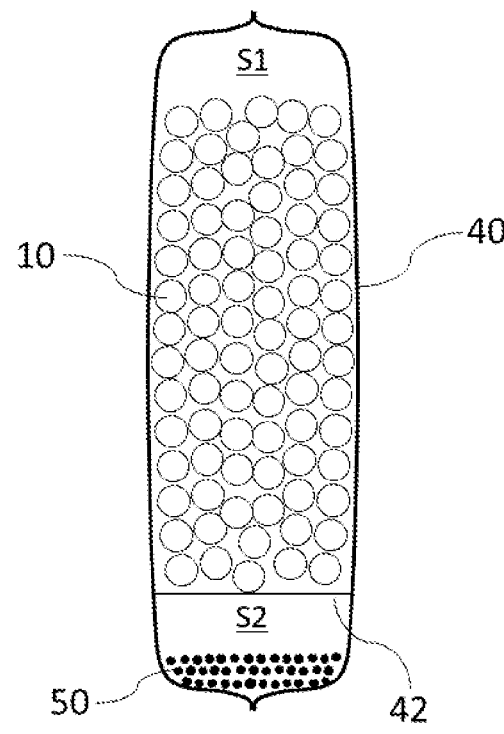

FIG. 4 is a front view showing a third embodiment of the excrement treatment material according to the present invention. Also, FIG. 5 is a schematic view showing an end face along a line V-V in FIG. 4. An excrement treatment material 3 is an excrement treatment material used for treating human or animal excrement, and includes the plurality of grains 10, a packaging bag 40, and an odor eliminating agent/deodorizing agent 50. In FIG. 4, for ease of viewing, the packaging bag 40 is shown being made transparent. The constitution of the grains 10 is as described in the first embodiment.

The plurality of grains 10 are housed in the packaging bag 40. The packaging bag 40 is provided with odor eliminating property or deodorizing property. In the present embodiment, the odor eliminating agent/deodorizing agent 50 is housed in the packaging bag 40. The odor eliminating agent/deodorizing agent 50 is composed of an odor eliminating agent or a deodorizing agent. That is, the odor eliminating agent/deodorizing agent 50 may be composed of both of the odor eliminating agent and the deodorizing agent, or may be composed of only either one of the odor eliminating agent or the deodorizing agent. As the odor eliminating agent or the deodorizing agent, respectively, the metal or the porous material described above can be used.

The odor eliminating agent/deodorizing agent 50 is housed in the packaging bag 40 in a state of being apart from the plurality of grains 10. In detail, the packaging bag 40 is provided with a partition member 42. The partition member 42 partitions the interior of the packaging bag 40 into a space S1 (first space) and a space S2 (second space). The space S1 is a space surrounded by a part of the packaging bag 40 (a part above the partition member 42) and the partition member 42. The space S2 is a space surrounded by a part of the packaging bag 40 (a part below the partition member 42) and the partition member 42. The plurality of grains 10 are housed, among the space S1 and the space S2, only in the space S1. That is, all grains 10 are housed in the space S1. On the other hand, the odor eliminating agent/deodorizing agent 50 is housed, among the space S1 and the space S2, only in the space S2. That is, all odor eliminating agent/deodorizing agent 50 is housed in the space S2.

The partition member 42 is provided near the lower end of the packaging bag 40. Specifically, the distance from the partition member 42 to the lower end of the packaging bag 40 is smaller than the distance from the partition member 42 to the upper end of the packaging bag 40. Thus, the volume of the space S2 is smaller than the volume of the space S1.

Figure 6:
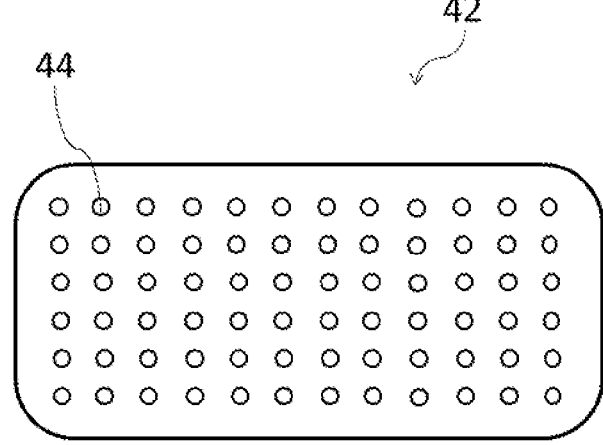
FIG. 6 is a plan view showing an example of a partition member 42.
Figure 7:
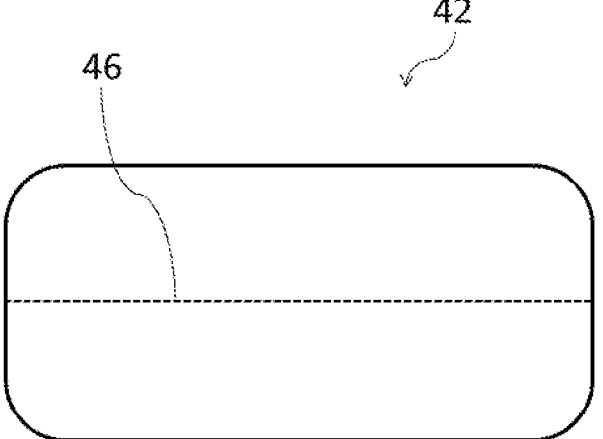
FIG. 7 is a plan view showing another example of the partition member 42.

The space S1 and the space S2 may be in communication with each other, or may not be in communication with each other. In the former case, the partition member 42 is provided with, for example, a hole 44 having a size that allows neither the grains 10 nor the odor eliminating agent/deodorizing agent 50 to pass through the hole 44 as shown in FIG. 6. In the latter case, the partition member 42 is preferably provided with a cutting line 46 as shown in FIG. 7. By cutting the partition member 42 along the cutting line 46, an opening having a size that allows both the grains 10 and the odor eliminating agent/deodorizing agent 50 to pass through the opening is formed in the partition member 42. By housing used grains 10 in the packaging bag 40 again after cutting the partition member 42 in this way, the grains 10 and the odor eliminating agent/deodorizing agent 50 can be mixed in the packaging bag 40. The cutting line 46 is, for example, perforations.

Note that the packaging bag 40 may be made of a raw material that contains an odor eliminating agent or a deodorizing agent similarly with the packaging bag 20. Also, an odor eliminating agent or a deodorizing agent may adhere to the inner surface of the packaging bag 40 similarly with the packaging bag 30.

Next, an example of a method for manufacturing the excrement treatment material 3 will be described as a third embodiment of the method for manufacturing an excrement treatment material according to the present invention. This manufacturing method includes a grain forming step, an odor eliminating agent/deodorizing agent housing step, and a grain housing step. The contents of the grain forming step are as described in the first embodiment.

The odor eliminating agent/deodorizing agent housing step is a step of housing the odor eliminating agent/deodorizing agent 50 in the packaging bag 40. In this step, a powdery or granular odor eliminating agent/deodorizing agent 50 is housed in the packaging bag 40 in a state that the lower end portion of the packaging bag 40 is open with a filling machine or the like. After that, the lower end portion of the packaging bag 40 is closed. Thus, the odor eliminating agent/deodorizing agent 50 is housed in the space S2 of the packaging bag 40. In the present embodiment, the odor eliminating agent/deodorizing agent 50 is housed in the packaging bag 40 in a state of being apart from the plurality of grains 10 in this way.

The grain housing step is a step of housing the plurality of grains 10 formed in the grain forming step in the packaging bag 40. In this step, a predetermined amount of the grains 10 is housed in the packaging bag 40 in a state that the upper end portion of the packaging bag 40 is open with a filling machine or the like. After that, the upper end portion of the packaging bag 40 is closed. Note that the odor eliminating agent/deodorizing agent housing step and the grain housing step may be performed in arbitrary order. Accordingly, the excrement treatment material 3 is obtained.

Furthermore, an example of a method for utilizing the excrement treatment material 3 will be described as another embodiment of the method for utilizing an excrement treatment material according to the present invention. This utilizing method includes an excrement treating step, and a grain re-housing step.

The excrement treating step is a step of taking out the plurality of grains 10 from the packaging bag 40 to use the plurality of grains 10 for treatment of excrement. In this step, for example, after the plurality of grains 10 are taken out from the space S1 by opening the upper end portion of the packaging bag 40, the grains 10 are placed in a box-shaped toilet so that humans or animals can excrete on the grains 10. At this time, the lower end portion of the packaging bag 40 is not opened, and the odor eliminating agent/deodorizing agent 50 is not taken out from the space S2.

The grain re-housing step is a step of housing the plurality of grains 10 that have been used in the excrement treating step in the packaging bag 40 again. In this step, for example, the used grains 10 are picked up from the toilet and put back into the packaging bag 40 with a scoop or the like. In the case where the partition member 42 is provided with the cutting line 46, the partition member 42 is cut along the cutting line 46 prior to putting back the used grains 10. Thus, the used grains 10 can be disposed of in a state of being housed in the packaging bag 40.

Advantageous effects of the present embodiment will be described. In the present embodiment, the packaging bag 40, which is provided with odor eliminating property or deodorizing property, is used. For this reason, in the excrement treatment material 3, by disposing of used grains 10 in a garbage box or the like in a state in which the grains 10 are housed in the packaging bag 40, it is possible to reduce an odor generating from excrement adhering to the grains 10 while confining the odor in the packaging bag 40. Thus, the odor becomes less likely to diffuse around. Accordingly, the excrement treatment material 3 that is suitable for making an odor less likely to diffuse around after disposal, and methods for manufacturing and utilizing the same are implemented.

The odor eliminating agent/deodorizing agent 50 is housed in the packaging bag 40. Thus, it is possible to implement the packaging bag 40 that is provided with the odor eliminating property or the deodorizing property without using a raw material that contains an odor eliminating agent or a deodorizing agent as the raw material of the packaging bag 40, or particularly processing the packaging bag 40. Also, in the case where the packaging bag 40 is made of the raw material that contains an odor eliminating agent or a deodorizing agent, or in the case where an odor eliminating agent or a deodorizing agent adheres to the inner surface of the packaging bag 40, it is possible to enhance the odor eliminating property or the deodorizing property of the packaging bag 40.

The odor eliminating agent/deodorizing agent 50 is housed in the packaging bag 40 in a state of being apart from the plurality of grains 10. Thus, it becomes easier to take out only the grains 10 selectively from the packaging bag 40 with the odor eliminating agent/deodorizing agent 50 remaining in the packaging bag 40. Other effects of the excrement treatment material 3 are the same as the excrement treatment materials 1, 2.

The present invention is not limited to the above-described embodiments, and various modifications can be made. In the above-described embodiments, an example is given in which the grains 10 have a multilayer structure composed of the core portion 12 and the coating portion 14. However, it is not essential to provide the coating portion 14. That is, the grains 10 may have a single-layer structure composed only of the core portion 12. In that case, the core portion 12 preferably contains an adhesive material.

In the above-described embodiments, an example is given in which the water-absorbing grains 10 treat excrement by absorbing the excrement. However, the grains 10 may be water-permeable grains that treat excrement by allowing the excrement to pass therethrough. Here, there are two types of water-permeable grains, one in which the excrement passes through the interior of the grains, and another in which the excrement passes through a gap between the grains. Examples of the latter type include grains having water repellency.

LIST OF REFERENCE NUMERALS

1 Excrement Treatment Material
2 Excrement Treatment Material
3 Excrement Treatment Material
10 Grain
12 Core Portion
14 Coating Portion
20 Packaging Bag
30 Packaging Bag
40 Packaging Bag
42 Partition Member
44 Hole
45 Cutting Line
50 Odor Eliminating Agent/Deodorizing Agent

The invention claimed is:

1. An excrement treatment material comprising:
a plurality of grains for treating excrement; and
a packaging bag in which the plurality of grains are housed,
wherein the packaging bag consists of an odor eliminating agent or a deodorizing agent,
wherein the grains for treating excrement have a core-coating structure, wherein the core has a granular shape and is comprised of organic matter that absorbs and retains moisture of the excrement and is selected from the group consisting of paper, used tea leaves, plastic, and bean curd lees, and
wherein the coating on the core is comprised of an adhesive material that fully or partially coats the core.

2. The excrement treatment material according to claim 1, wherein the odor eliminating agent contains a metal that functions as the odor eliminating agent.

3. The excrement treatment material according to claim 2, wherein the metal is copper.

4. The excrement treatment material according to claim 1, wherein the deodorizing agent contains a porous material that functions as the deodorizing agent.

5. The excrement treatment material according to claim 4, wherein the porous material is organic matter.

6. The excrement treatment material according to claim 5, wherein the organic matter is coffee-extracted grounds or used tea leaves.

7. The excrement treatment material according to claim 1, wherein an additional odor eliminating agent or deodorizing agent is adhered to an inner surface of the packaging bag.

8. The excrement treatment material according to claim 1, wherein an additional odor eliminating agent or deodorizing agent is housed in the packaging bag.

9. The excrement treatment material according to claim 8, wherein the additional odor eliminating agent or deodorizing agent is housed in the packaging bag in a state of being apart from the plurality of grains.

10. A method for manufacturing an excrement treatment material, the method comprising:
a grain forming step of forming a plurality of grains for treating excrement, the grains for treating excrement having a core-coating structure, wherein the core has a granular shape and is comprised of organic matter that absorbs and retains moisture of the excrement and is selected from the group consisting of paper, used tea leaves, plastic, and bean curd lees, and wherein the coating on the core is comprised of an adhesive material that fully or partially coats the core; and
a grain housing step of housing the plurality of grains formed in the grain forming step in a packaging bag, wherein the packaging bag consists of an odor eliminating agent or a deodorizing agent.

11. The method for manufacturing an excrement treatment material according to claim 10, wherein the odor eliminating agent contains a metal that functions as the odor eliminating agent.

12. The method for manufacturing an excrement treatment material according to claim 10, wherein the deodorizing agent contains a porous material that functions as the deodorizing agent.

13. The method for manufacturing an excrement treatment material according to claim 12, wherein the porous material is organic matter.

14. The method for manufacturing an excrement treatment material according to claim 10, wherein an additional odor eliminating agent or deodorizing agent is adhered to an inner surface of the packaging bag.

15. The method for manufacturing an excrement treatment material according to claim 14, the method further comprising:

an inner surface processing step of making the additional odor eliminating agent or deodorizing agent adhere to the inner surface of the packaging bag prior to the grain housing step.

16. The method for manufacturing an excrement treatment material according to claim 10, the method further comprising:

an odor eliminating agent/deodorizing agent housing step of housing an additional odor eliminating agent or a deodorizing agent in the packaging bag.

17. The method for manufacturing an excrement treatment material according to claim 16, wherein in the odor eliminating agent/deodorizing agent housing step, the additional odor eliminating agent or deodorizing agent is housed in the packaging bag in a state of being apart from the plurality of grains.

* * * * *